United States Patent [19]

Jarrell

[11] Patent Number: 4,824,169
[45] Date of Patent: Apr. 25, 1989

[54] ORTHOPEDIC SEAT

[76] Inventor: Loyd E. Jarrell, 2920 Sandstone Trail, Marietta, Ga. 30064

[21] Appl. No.: 160,243

[22] Filed: Feb. 25, 1988

[51] Int. Cl.[4] ................................................. A47C 7/02
[52] U.S. Cl. ..................... 297/230; 297/284; 297/314; 297/458
[58] Field of Search ............... 297/230, 231, 255, 256, 297/219, 284, 458, 459, 460, 314

[56] References Cited

U.S. PATENT DOCUMENTS

| | | | |
|---|---|---|---|
| D. 116,558 | 9/1939 | Ficks . | |
| 1,379,771 | 5/1921 | McKinley | 297/314 |
| 1,640,743 | 8/1927 | Yuhasz . | |
| 1,802,853 | 4/1931 | Weltner | 297/458 |
| 1,891,747 | 12/1932 | Clements . | |
| 2,034,369 | 3/1936 | Bayer | 5/344 |
| 2,047,035 | 7/1936 | Rosenberg | 190/42 |
| 2,557,874 | 6/1951 | Kailenta | 297/256 |
| 2,591,306 | 4/1952 | Sherman | 297/230 |
| 2,672,920 | 3/1954 | Altgelt | 297/314 |
| 2,816,599 | 12/1957 | Adams . | |
| 2,884,991 | 5/1959 | Bloomquist . | |
| 3,265,437 | 8/1966 | Mincieli | 297/231 |
| 3,495,871 | 2/1970 | Resag et al. | 297/284 |
| 3,511,537 | 5/1970 | Ackermann | 297/458 |
| 3,542,421 | 11/1970 | Ambrose | 297/230 |
| 4,105,249 | 8/1978 | Van Vliet, Jr. | 297/230 |
| 4,190,918 | 3/1980 | Harvell | 5/465 |
| 4,362,334 | 12/1982 | Ross et al. | 297/230 |
| 4,506,929 | 3/1985 | Josefek | 297/230 |
| 4,556,254 | 12/1985 | Roberts | 297/460 |
| 4,565,405 | 1/1986 | Mayer | 297/230 |
| 4,718,724 | 1/1988 | Quinton et al. | 297/230 |

*Primary Examiner*—Francis K. Zugel
*Attorney, Agent, or Firm*—Thomas & Kennedy

[57] ABSTRACT

A portable orthopedic seat has a backing sheet adapted to be draped over the top and back of a chair, a wedge-shaped and a half-teardrop shaped cushion, and fasteners for releasibly fastening the cushions to the backing sheet in orientations selected to adapt the chair for use by a person with a specific abnormal spinal condition.

3 Claims, 3 Drawing Sheets

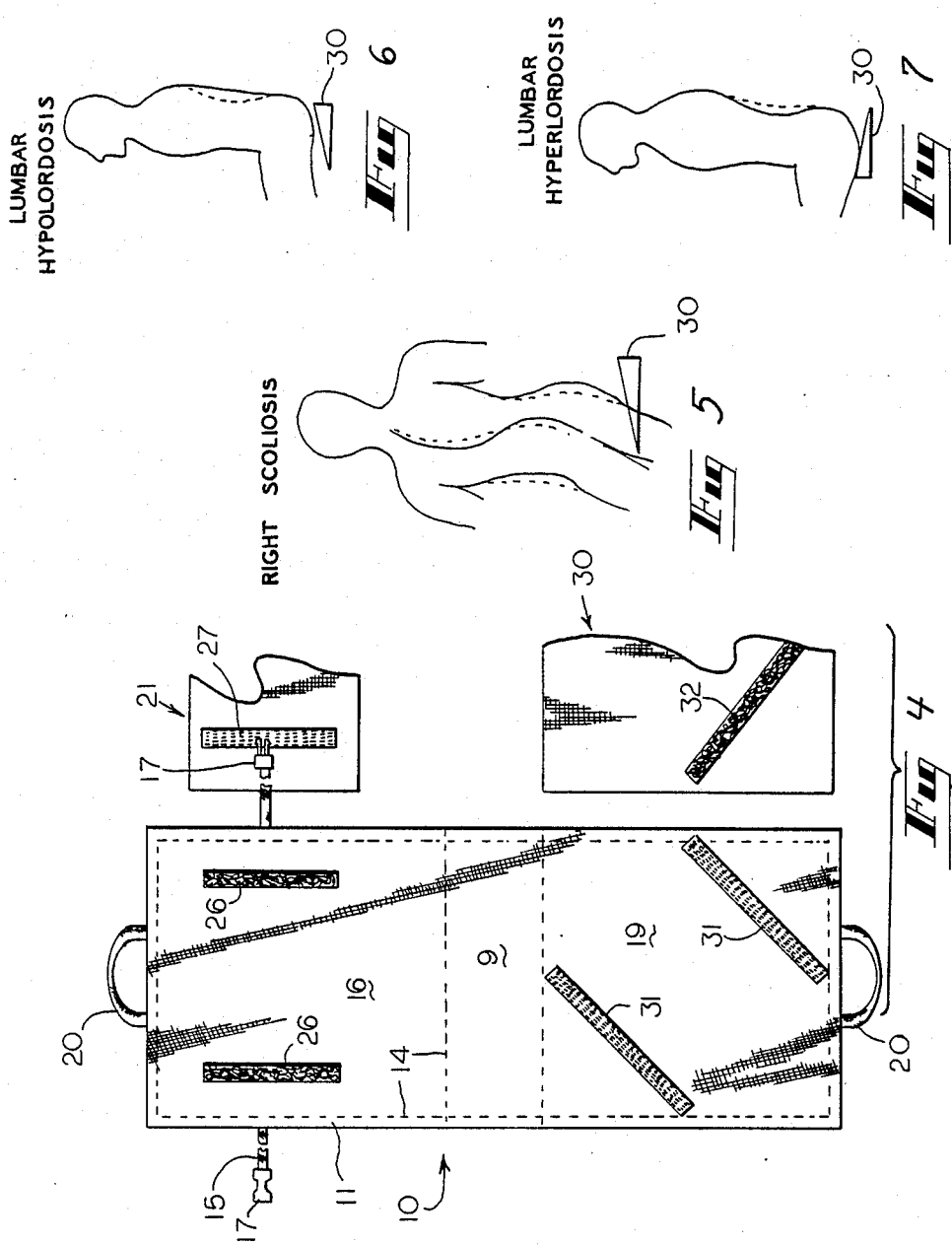

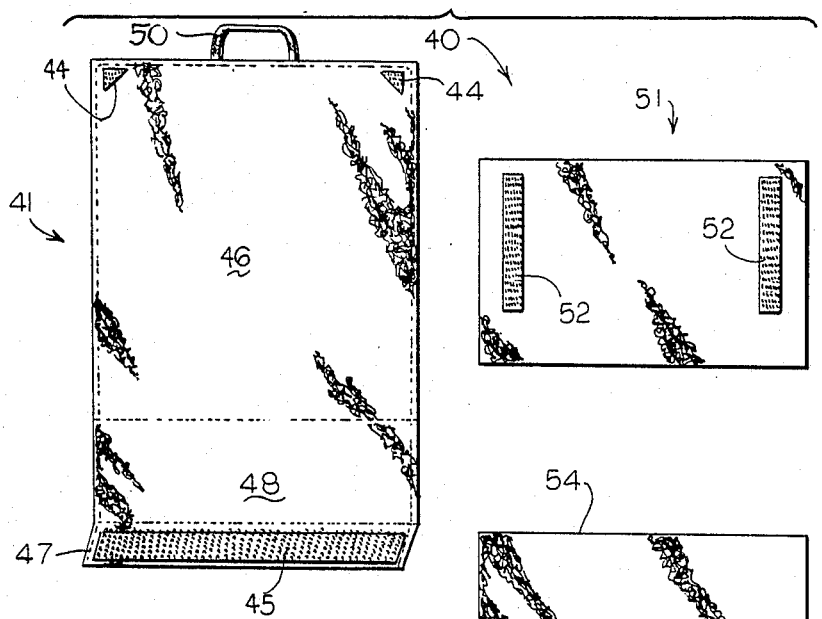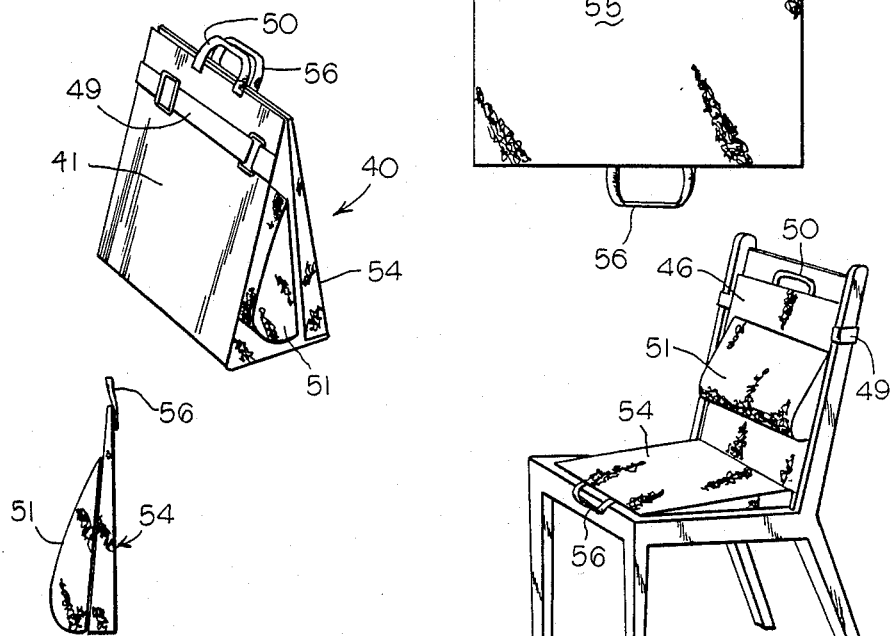

ORTHOPEDIC SEAT

TECHNICAL FIELD

This invention relates generally to orthopedic seats of a type designed to be carried and placed upon chairs to recontour them temporarily to support persons with an abnormal spinal condition or to maintain normal spinal curvatures.

BACKGROUND OF THE INVENTION

Heretofore, orthopedic seats have been devised for use in adapting conventional chairs and the like for use by people having spinal abnormalities. Exemplary of such are those seats shown in U.S. Pat. Nos. 1,891,747 and 4,362,334. In general these seats have been designed with two criteria principally in mind. Firstly, they have been designed so as to be easily carried and mounted to a conventional chair. Secondly, they have been designed to provide a support that conforms to the abnormal body condition or posture of the individual users so that support contact is provided over relatively large areas of the thighs, buttocks, and back of the user while seated upon conventionally contoured chairs or the like.

Some common abnormal spinal conditions are illustrated in FIGS. 5-7 of the drawings. Scoliosis is abnormally lateral curvature of the spine. A right scoliosis condition is illustrated in FIG. 5. A left scoliosis abnormality would, of course, curve in the opposite lateral direction. Where the spine is too straight, i.e. with the spine insufficiently curved in the lordotic direction, the condition is referred to as hypolordosis, which is illustrated in FIG. 6. Conversely, where excessive forward curvature is present, i.e. with the spine insufficiently curved in the kyphodic direction, as shown in FIG. 7, the condition is known as hyperlordosis. In these figures normal curvature is illustrated in broken lines while the actual shape of the individual with the abnormality is shown in solid lines.

Though reconfiguring conventional seats so as to provide direct body contact over a greater portion of the person is helpful, it would be of far greater benefit if the body itself were to be supported in a manner so as to reposition the spine from any abnormal orientation towards a normal orientation, or to maintain a normal orientation. It is to the provision of such an orthopedic seat that the present invention is therefore primarily directed.

SUMMARY OF THE INVENTION

In one form of the invention, a portable orthopedic seat comprises a backing adapted to be placed upon at least a portion of the seat and upon the back of a chair with a fold which separates back and seat portions of the backing, located adjacent the junction of the chair seat and back. A wedge-shaped seat cushion is provided that is adapted to be positioned upon the backing seat portion in various orientations with respect thereto. A half-teardrop shaped lordotic cushion is also provided which is adapted to be positioned upon the backing back portion in various orientations with respect thereto. Fastening means are also provided for releasibly fastening the lordotic cushion in various orientations to the back portion of the backing.

In another form of the invention a portable orthopedic seat comprises a backing sheet of a length sufficient to be draped over the seat and back of a chair and with a handle affixed to an end thereof. The seat has a wedge-shaped cushion and means releasibly fastening the cushion to the backing sheet in a plurality of orientations. A belt is attached to the backing sheet of a length sufficient to be wrapped about the back of a chair to secure the seat to the chair and to be wrapped about the flexible sheet with the sheet folded about the cushion in a packed configuration for hand carrying.

In yet another form of the invention a method of temporarily adapting a chair for use in supporting a person with an abnormal spinal condition comprises the steps of draping a backing sheet over at least a portion of the top of the chair seat and over the front of the chair back. The backing sheet is fastened to the chair. A cushion is then releasibly attached to the backing sheet in a position and orientation to accommodate the abnormal spinal condition of the person while seated upon the adapted chair.

BRIEF DESCRIPTION OF THE DRAWING

FIG. 4 is a plan view of the orthopedic seat illustrated in FIG. 1 with the seat cushions located to one side of the seat backing sheet and overturned to reveal fastening means for securing the cushions to the backing sheet.

FIG. 5 is a schematic diagram of a person suffering from right scoliosis of the lumbar spine.

FIG. 6 is a schematic diagram of a person suffering from hypolordosis of the lumbar spine.

FIG. 7 is a schematic diagram of a person suffering from hyperlordosis of the lumbar spine.

FIG. 8 is plan view of a portable orthopedic seat embodying principles of the invention in another form with the seat cushions located to one side of the seat backing sheet and overturned to reveal fastening means.

FIG. 9 is a perspective view of the orthopedic seat shown in FIG. 8 in a folded configuration for hand carrying or storage.

FIG. 10 is a side view of the two seat cushions shown mounted together for carrying.

FIG. 11 is a perspective view of the orthopedic seat illustrated in FIG. 8 shown mounted on a chair with its cushions oriented for use by one suffering from lumbar hypolordosis.

DETAILED DESCRIPTION

Figure 1:
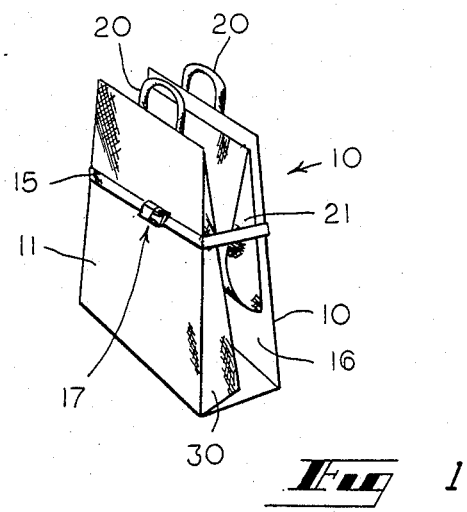
FIG. 1 is a perspective view of a portable orthopedic seat embodying principles of the present invention with the seat shown in a folded configuration for hand carrying or storage.
Figures 2, 3:
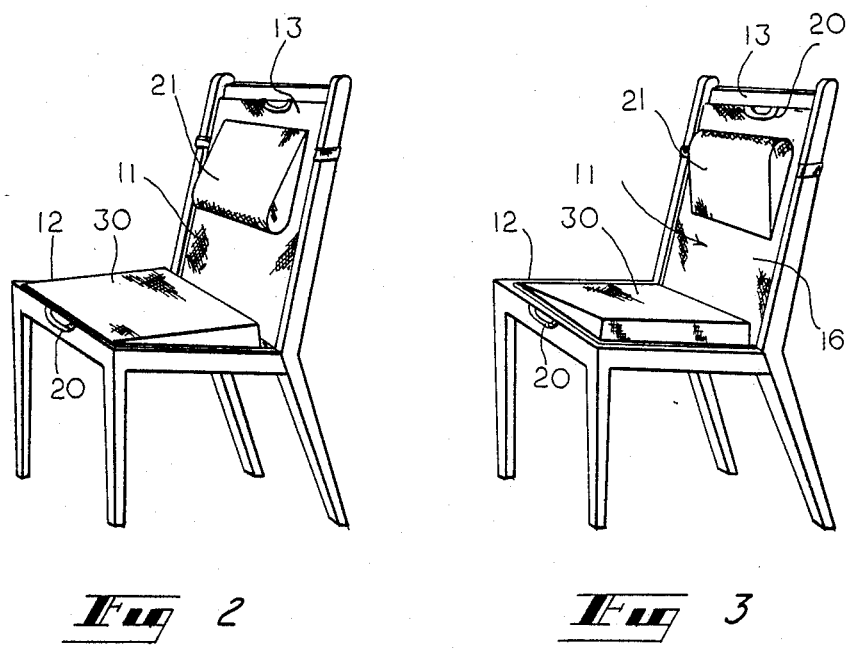
FIG. 2 is a perspective view of the orthopedic seat illustrated in FIG. 1 shown mounted upon a chair for use.
FIG. 3 is another perspective view of the orthopedic seat illustrated in FIG. 1 shown mounted upon a chair for use with the seat cushions in a different orientation from that shown in FIG. 2.

With reference next to the drawings, there is shown in FIGS. 1-4 a portable orthopedic seat 10 having a fabric type backing sheet 11 which is sized and configured to be draped over the seat and back of a chair. Sheet 11 has a seat portion 12 and a back portion 13, as shown in FIGS. 2 and 3. In this specific example the backing sheet measures 32 inches long by 13 inches wide. The backing sheet is made of two plys of fabric sewn together by stitches 14. A two-piece elastic belt or strap 15 is secured to an upper portion 16 of the backing sheet. Conventional quick-release snap-on fasteners 17 are mounted to each end of the belt so that they can be releasibly held together. The belt is of a length sufficient to enable it to be looped behind and adjusted to the back of the chair to secure the backing sheet portion 16 uprightly to the back of the chair. Its length is also sufficient to enable it to be looped about a lower portion 19 of the backing sheet, that is adapted to be placed upon the seat 12 of a chair, in a compacted, folded configuration with cushions supported thereon, as shown in FIG. 1. An approximately square, unshown, thin panel is sandwiched between the two fabric plys of the backing sheet in the upper portion 19 to render it relatively stiff. The intermediate backing portion 9 has no panel so that it is flexible. The lower portion 19 derives it rigidity from a high density urethane foam insert cushion. A handle 20 is secured to each end of the backing sheet for hand carrying the seat when it is in its compacted configuration.

With continued reference to the drawing, the orthopedic seat is further seen to include a back or lordotic cushion 21 which is generally half-teardrop shaped and which is adapted to be fastened to the upper portion 16 of the backing sheet 11 in various orientations and with substantial latitude in its position. It is releasibly fastened to the backing sheet by means of strips bearing mutually interlockable fibers such as that sold under the name Velcro. Specifically, the fastening means includes two strips 26 of Velcro that are mounted in mutually parallel relation permanently to the backing sheet portion 16, as shown in FIG. 4. Two other strips of Velcro 27 are permanently mounted to the back cushion 21 in mutually spaced, parallel relation for releasible engagement with the other strips 26. It should be understood that with this geometry the cushion 21 can be mounted with the mating strips of Velcro so that its thicker end is located above its thinner end, as shown in FIG. 3, or with its thicker end located below its thinner end, as shown in FIG. 2. The cushion 21 here measures 13 by 20 inches with a rise of from 0.5 inch thickness at its thinner end to 3.5 inches in thickness at the opposite end.

The orthopedic seat also has a wedge-shaped bottom or pelvic lift cushion 30 which is adapted to be releasibly fastened to the bottom portion 19 of the backing sheet. Again, strips of Velcro are used as the fastening means. From FIG. 4 the fastening means is seen to include two strips 31 attached along catercorners of the bottom portion of the backing in mutually parallel relation for mating engagement with two other Velcro strips 32 that are shown mounted catercorneredly to the cushion 30. With this orientation and equal spacings of the pairs of strips, the cushion 30 may be mounted to the lower portion 19 at four different rotary orientations 90° apart.

For example, the cushion 30 in FIG. 4 may be rotated 180° from that shown to bring bottom strip 32 on the cushion into mating engagement with the bottom strip 31 on the backing sheet. The upper strips will also become engaged. Full flush contact may also be had by inverting the cushion 180°. In one of the two intermediary 90° positions, only the end portions of the pairs of strips overlay each other. However, as this is the bottom cushion, this degree of contact is usually quite sufficient to hold the seat in place.

The orthopedic seat may be configured as shown in FIG. 1 for storage and transportation. Here it is seen that the backing sheet 11 is folded with the cushions 21 and 30 mounted upon the rigid sheet sections 16 and 19. Once folded, the belt 15 may be placed about the rear side of the seat portion 19 and the couplers 17 releasibly snapped closed whereupon the belt holds the assembly together with the two handles 20 positioned side by side. In this compact configuration the orthopedic seat may be hand carried from place to place for temporary use on chairs or similar body supports.

For usage the couplers 17 are unsnapped and the backing sheet draped upon the chair, as shown in FIGS. 2 and 3, with the upper portion 16 overlaying the front of the chair back 13 and with the lower portion 19 resting upon the chair seat 12. If either or both of the cushions are to be reoriented they are simply removed from the backing, reoriented, and reattached, as needed, to accommodate the specific abnormality of the user. For example, in FIG. 2 the seat cushion 30 is positioned with its thicker end adjacent the back of the chair and its thinner end positioned adjacent the front of the chair. As shown in FIG. 6 this position would be employed by one suffering from hypolordosis. In this position the cushion 30 is employed to urge the back to the more normally arched configuration shown by the broken lines. This is the same orientation that they had assumed in the stowed position of FIG. 1. Conversely, for someone suffering from hyperlordosis the cushion 30 would be reoriented 180° from that shown in FIG. 2.

The cushion 21 is shown in FIG. 2 positioned with its relatively thick end located closest to the seat cushion while in FIG. 3 it is located in an inverted position with its thick end located distally from the seat cushion. Again, this positioning is made with regard to the specific spinal condition of the user. One suffering from hyperkyphosis of the thoracic spine, which is similar to a hunched back configuration, would orient the cushion 21 as shown in FIG. 3. If desired, the cushion 21 may also function as a lordotic cushion for supine head support. In that event its thinner end is placed under the back of the head and its thicker end placed under the user's neck.

The seat cushion 30 may also be oriented with the thick and thin sides rotated 90° from that illustrated in FIG. 2. For example, a person suffering from right scoliosis, as shown in FIG. 5, would position the cushion so as to elevate the right buttocks with respect to the left to urge his or her back towards a more normal spinal shape. A person suffering from left scoliosis would, of course, orient it in the reverse direction. Following usage the seat may be reassembled into the compact configuration shown in FIG. 1 for storage or hand carrying.

With reference next to FIGS. 8-11, there is shown an orthopedic seat 40 that embodies principles of the invention in another preferred form. The seat 40 comprises a fabric type backing sheet 41 which is sized and shaped to be draped over the back of a chair and over a small portion of the chair seat located adjacent the chair back. It has a back portion 46, a seat portion 47 and an intermediate portion 48 that unitarily joins the back and seat portions together. Again the back and seat portions are substantially rigid while the intermediate portion is flexible.

As opposed to the embodiment of FIGS. 1-4, the inside surface of the back and intermediate portions, shown in FIGS. 8, is substantially all formed of Velcro loop type material. However, two small strips 44 of hook type Velcro are mounted adjacent the upper corners of the backing sheet back portion 46. Another hook type Velcor strip 45 is attached to the seat portion 47. The ends of an adjustable, elastic belt 49 are fastened to the sides of the back portion.

The orthopedic seat 40 also includes a back or lordotic cushion 51 of half-teardrop shape, in side profile. It bears two strips of Velcro 52 for mating engagement with the loop type Velcro material of the backing sheet back portion 46. A wedge-shaped seat cushion 54 is also provided where surface 55 is formed of Velcro loops. A handle 56 is fastened to its thinnest end.

The orthopedic seat may be mounted upon a chair as shown in FIG. 11 with the back portion 46 of the backing sheet held to the chair back by the belt 49 and with the small seat portion 47 laid atop the rear portion of the chair seat. The cushion 51 may then be releasably mounted at various elevations to the back portion by engagement of its Velcro strips 52 to the Velcro cover or ply of the backing sheet. The seat cushion 54 may be laid upon the chair seat and held in position by mating of the Velcro strip 45 to the cushion cover. Again, the orientation of the cushion 54 may be varied since all portions of it may be releasably interlocked with the Velcro strip 45.

The seat may be formed into the compact configuration shown in FIG. 9 for carrying or storage with handles 50 and 56 together. Alternatively, the two cushions only may be releasably mounted together as shown in FIG. 10 and carried by the single handle 56.

It thus is seen that a portable, orthopedic seat is provided which is of simple construction which may be easily configured in a compact configuration for storage and transportation and yet be easily mounted upon a chair for temporary use. The seat is extremely versatile in that it may be used to compensate for various spinal abnormalities in a manner that actually urges the spine back towards a more normal orientation rather than merely provide direct contact between person and support. It may also be used by people who do not have a congenital spinal abnormality.

It should be understood that the just described embodiments merely illustrate principles of the invention in two preferred forms. Many modifications, additions and deletions may therefore be made without departure from the spirit and scope of the invention as set forth in the following claims:

I claim:

1. A portable orthopedic seat comprising:
   a backing adapted to be placed upon the seat and back of a chair and having a fold which extends from a first side edge to a second side edge of said backing between back and seat portions of said backing;
   a generally wedge-shaped seat cushion having a narrower portion at one end and a thicker portion at an opposite end;
   a generally half-teardrop shaped lordotic cushion having a narrower portion at one end and a thicker portion at an opposite end;
   first fastening means comprising masses of interlockable fibers for releasibly fastening said seat cushion upon said seat portion of said backing in four different orientations with respect to said seat portion including a first orientation wherein said narrow portion is generally parallel and proximal to said fold, a second orientation wherein said narrow portion is generally parallel and distal to said fold, a third orientation wherein said narrow portion is generally perpendicular to said fold and proximal to said backing first side edge, and a fourth orientation wherein said narrow portion is generally perpendicular to said fold and proximal said backing second side edge; and
   second fastening means comprising masses of interlockable fibers for releasibly fastening said lordotic cushion upon said back portion of said backing in two orientations with respect to said back portion including a first orientation wherein said narrow portion of said lordotic cushion is generally parallel and proximal to said fold and a second orientation wherein said narrow portion of said lordotic cushion is generally parallel and distal to said fold;
   whereby the backing may be positioned upon a chair and the seat and lordotic cushions respectively fastened to the seat and back portions of said backing in orientations selected to accommodate the specific spinal abnormalities of the user.

2. The orthopedic seat of claim 1 wherein said first fastening means comprises a first pair of strips of Velcro material mounted to said backing back portion oriented generally parallel to each other and perpendicular to said fold, and a second pair of strips of Velcro material mounted to said lordotic cushion oriented generally parallel to each other and extending from said narrower end to said thicker end, and wherein said second fastening means comprises a third pair of strips of Velcro material mounted to said backing seat portion oriented generally parallel to each other and obliquely with respect to said fold, and a fourth pair of strips of Velcro material mounted to said seat cushion oriented generally parallel to each other and obliquely with respect to said narrower end whereby the first and second pairs of strips will overlay or traverse each other in all angular positions of the seat cushion with respect to the seat portion of the backer.

3. The seat as claimed in claim 1 further including a handle attached to an end of said backing distal from said fold and a belt of a length sufficient to be looped behind the chair to hold said backing thereto and of sufficient length to be looped behind said seat portion of said backing when folded into said folded configuration to hold the seat and back portions together for hand carrying by said handle.

* * * * *